United States Patent [19]
Jenkins

[11] 3,942,357
[45] Mar. 9, 1976

[54] INSPECTION APPARATUS

[76] Inventor: Anthony Jenkins, Analytical Instruments Ltd., Fowlmere, Royston, Hertfordshire, England

[22] Filed: July 15, 1974

[21] Appl. No.: 488,536

[30] Foreign Application Priority Data
May 2, 1974 United Kingdom........... 19207/74

[52] U.S. Cl. ................................................. 73/23
[51] Int. Cl.$^2$........................................ G01N 33/22
[58] Field of Search............... 73/23, 19, 27 R, 23.1; 340/237 R; 23/232 R, 254 R, 266; 55/158, 270

[56] References Cited
UNITED STATES PATENTS

| | | | |
|---|---|---|---|
| 2,745,282 | 5/1956 | Rochon............................. | 73/19 X |
| 3,229,500 | 1/1966 | Kraus................................ | 73/23 |
| 3,430,482 | 3/1969 | Dravnieks et al................. | 73/23.1 |
| 3,531,980 | 10/1970 | Pennucci............................ | 73/19 |
| 3,617,734 | 11/1971 | Chaudet............................. | 73/23 |
| 3,660,034 | 5/1972 | Baranyi et al.................... | 73/19 |
| 3,681,032 | 8/1972 | Long.................................. | 73/23 |
| 3,765,842 | 10/1973 | Purt .................................. | 340/237 R |

FOREIGN PATENTS OR APPLICATIONS 200,872   10/1967   U.S.S.R................................. 73/19

Primary Examiner—Richard C. Queisser
Assistant Examiner—Stephen A. Kreitman
Attorney, Agent, or Firm—Woodhams, Blanchard and Flynn

[57] ABSTRACT

An apparatus for checking the contents of closed containers, such as baggage, for the presence of substances, such as explosives and drugs, which are capable of emitting characteristic vapours. The baggage is located in a compartment having means to promote the diffusion of the vapours out of the baggage and into the compartment. Such means can be by vacuum pumping, by vibration of the atmosphere within the compartment or a combination of both. The vapours diffusing into the compartment are drawn at substantially constant flow rate into a detector assembly sensitive to the presence of the vapours. Initially the concentration of vapours in the atmosphere evacuated from the compartment is low and a major proportion of this evacuated flow by-passes the detector assembly. As the pressure in the compartment is reduced there is an increase in the concentration of the vapours in the atmosphere and at a lower pressure limit all the exhaust from the compartment passes into the detector.

10 Claims, 1 Drawing Figure

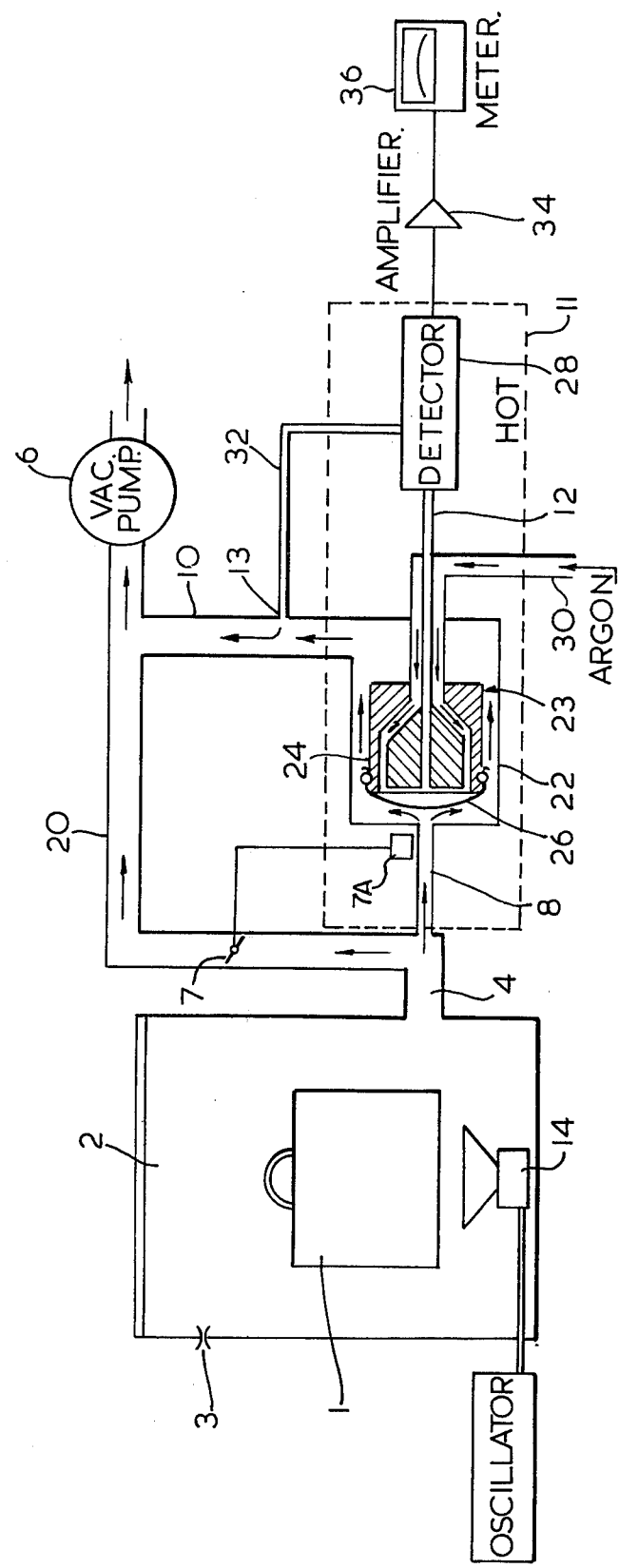

INSPECTION APPARATUS

The present invention concerns an apparatus for checking the contents of closed containers, such as suitcases, crates and the like, for gaseous content.

It is known for this purpose to arrange a closed container under test in a chamber and to reduce the pressure in the chamber to enable any vapours to escape from the interior of the container into the chamber and then into an appropriate detector in communication with the chamber. It is assumed that the containers under test are not perfectly sealed so as to enable the vapours to diffuse into the chamber. However if the checking is to be accomplished in a short time period, and this is necessary when a large number of containers are to be checked individually, it is required to employ a high pumping rate to produce a rapid reduction in the pressure in the chamber. The present invention seeks to provide an apparatus which can rapidly and thoroughly check a large number of separate items, such as baggage at an airport for loading on to an aircraft.

According to the present invention an apparatus for checking the contents of closed containers, hereinafter termed baggage, for the presence of substances which are capable of emitting vapours comprises a compartment to receive the baggage, means to assist the diffusion of vapours out of the baggage into the compartment and means for controlling the vapours to flow at a substantially constant rate to a detector assembly sensitive to the presence of the vapours.

Preferably, the means to assist the diffusion of vapours out of the baggage comprises vacuum pumping of the compartment or vibration of the atmosphere within the compartment or a combination of both. Vibration can occur at a frequency in the range from sub-sonic through sonic to ultrasonic. The effect of vibrating the atmosphere within the chamber is to increase the diffusion rate of vapour from within the baggage. The vibrations can be generated by means of a transducer positioned within the compartment, or the wall of the compartment.

Preferably, when vacuum pumping, in order to provide a high pumping rate and consequently a rapid evacuation of the chamber, a major part of the evacuated flow initially by-passes the detector assembly, valve means being provided and operable to maintain a substantially constant flow into the detector assembly during evacuation of the chamber.

The invention will be described in further detail and by way of example with reference to the accompanying diagrammatic drawing.

An article under test, such as a suitcase 1, is placed within a compartment 2. The suitcase 1 can be supported on a platform, for example a grid, within the compartment 2 and the compartment is then closed and sealed. A venting port 3 is provided in a side wall of the compartment and the compartment is connected through an exhaust port 4 to a conduit system leading to a vacuum pump 6.

As shown, a branch 20 of the conduit system leads directly to the pump 6. A second branch 8, of smaller cross-section than the port 4 and the branch 20, leads from the port 4 into a chamber 22 accommodating a sampling probe 23. The chamber 22 is in turn connected through a further passageway 10 to the first branch 20 in front of or upstream of the pump 6.

The sampling probe 23 comprises a head portion 24 having its open end facing the branch passage 8 closed by a membrane 26. The membrane is chosen to have a greater permeability to the trace gas or gases to be detected than to other electron capture material, such as oxygen, present in the atmosphere. For example, a membrane which is selectively permeable to the vapours emitted by nitro-compounds found in explosives is a silastomer such as, methyl silicone elestomer. The volume to the rear of the membrane communicates through a conduit 12 with a detector 28, such as an electron capture detector. This is a detector which is sensitive to the presence of electron absorbers and in effect comprises an ionisation chamber containing a source of $\beta$ radiation, such as a tritium foil or $Ni_{63}$. A carrier gas, which is a non-electron absorber, is introduced into the volume behind the membrane 26 through a duct 30 and sweeps any gas or gases which pass through the membrane 26 into the detector. A convenient carrier gas is Argon although it will be appreciated that other gases which are non-electron absorbers such as nitrogen, can also be used. The detector exhaust is connected through a duct 32 to the passageway 10. The vacuum pump 6 therefore in addition to exhausting the compartment 2 also maintains a flow through the detector. The detector output is amplified by an amplifier 34 and registered on a meter or other indicating device 36. The portion of the apparatus within the dotted outline, that is the chamber 22 containing the probe 23 and the detector 28, is maintained at an elevated temperature which can be controlled by thermostats. It is desirable to maintain the portion within the dotted outline at an elevated temperature in order to reduce the possibility of trace gases clinging to the walls of the apparatus. The temperature will depend upon the particular trace gas to be detected but a typical temperature range can be from 75°C to above 150°C.

A throttle valve 7 is arranged within the branch 20, the valve being controlled either mechanically or automatically, in response to means 7A within the branch 8.

In operation, in order to reduce to a minimum the time taken to check a suitcase deposited within the compartment 2, it is necessary to set the vacuum pump at a very high pumping rate, for example 50 to 100 cubic feet per minute. It is required to reduce the pressure within the compartment 2 to a lower pressure at which any vapours emanating from an object within the suitcase 1 can escape into the compartment and preferably this should take place in a matter of seconds. Conveniently the reduction in pressure should take place in less than 10 seconds and preferably in less than 5 seconds. However the air flow out of the compartment resulting from this high pumping rate can, if passed over the membrane, cause a cooling of the membrane. Temperature changes of the membrane can result in changes in the diffusion rates of gases through the membrane. It is necessary to avoid such changes in diffusion rates as this can lead to spurious or inaccurate signals from the detector. For example an electron capture detector is sensitive to the presence of oxygen and the diffusion rate of oxygen through a membrane can vary with changes in temperature. This can cause a change in the output of the detector which could mask any response from the presence of the vapour or vapours of interest.

The invention overcomes this difficulty by maintaining a substantially constant flow rate over the membrane whereby to maintain a substantially constant temperature at the membrane. The heater compartment surrounding the membrane and detector further protects the system from changes and fluctuations in ambient temperature.

Initially the valve 7 is open and during the initial stages of evacuation most of the air extracted from the compartment 2 passes along the branch 20 to the pump 6. As the pressure within the compartment drops any vapour or vapours within the suitcase 1 will seep into the compartment and the maximum concentration of vapour or vapours in the compartment will occur at the lower limit of pressure. When the pressure within the compartment reaches its lower limit the valve 7 is actuated to close the branch 20 to enable all the exhaust from the compartment to enter the branch 8 and to flow over the membrane 26. The vapour or vapours if present can diffuse through the membrane and are swept into the detector by the carrier gas flow.

The flow down the branch 8 and across the membrane is maintained substantially constant by sensing the differential pressure along the branch 8 and adjusting the valve 7 accordingly. The valve adjustment can be achieved either electrically or mechanically in a servo-system.

The restricted entry port 3 to the compartment permits just sufficient air to enter the compartment to maintain the pressure therein at its lower limit when the valve 7 is actuated to close or substantially close the branch 20.

During the evacuation of the compartment a reduction in pressure occurs in front of the membrane and this can lead to an undesired ballooning and possible bursting of the membrane. This danger can be avoided by connecting the detector exhaust to the passageway 10 and as indicated by the reference numeral 13. The detector is connected directly through the conduit 12 to the rear of the membrane 26. As a result the pressures at the opposite sides of the membrane are substantially equal at all times during operation.

It is possible to extract vapour or vapours from the interior of the case by locating a transducer 14 within the compartment. The transducer can be actuated by an oscillator and can be operated to vibrate the air within the container at a frequency which can be infrasonic, sonic or ultra-sonic. It has been found that the vibration of the air in the compartment increases the diffusion rate of any vapour or vapours present in the suitcase. This oscillatory pumping of the air within the compartment can be used alone, that is without the need to evacuate the container, for the detection of vapour or vapours emitted from within the case. However it is preferable to use the oscillatory pumping technique in combination with the vacuum pumping of the compartment.

Finally, as an additional check on the contents of the case, an X-ray apparatus can be incorporated with the apparatus. For example, with reference to the illustrated embodiment an X-ray transmitter can be located at one side of the compartment to direct a stream of X-rays through the case and on to a screen located at the opposite side of the compartment. In this way the contents of the case can be inspected without opening the suitcase and simultaneously with the vapour detection step.

An electron capture detector can detect the presence of vapours emanating from nitro-compounds such as explosives but as previously mentioned such a detector is also sensitive to oxygen and as a result the atmospheric oxygen could mask any signals resulting from the presence of explosives. Consequently it is desirable to employ some means, such as the selectively permeable membrane, to ensure that the trace gas of interest and not oxygen is the predominating detectable component flowing into the detector. However the invention can be employed to detect the presence of other substances such as drugs which also exude characteristic vapours which can be detected in an appropriate detector. The invention is not restricted to use with an electron capture detector assembly. Examples of other forms of detector are the argon ionisation and the flame ionisation detectors. Whilst the detector system employed can be selectively chosen to meet particular operational requirements it is necessary to ensure that detectable amounts of the vapours or trace gases are conveyed in as short a time as possible into the detector in order to achieve a rapid check of a large number of containers, such as baggage and the like.

I claim:

1. Apparatus for checking the contents of closed containers for the presence of substances which are capable of emitting vapours comprising a compartment to receive the containers, means to promote the rapid diffusion of vapours out of the container into the compartment, a detector assembly sensitive to the presence of the vapours and connected to said compartment by a flow path so as to receive at least a proportion of the vapours diffusing into the compartment, means selectively permeable to the vapours and located in the flow path to the detector assembly, and means for maintaining the selectively permeable means at a constant temperature.

2. Apparatus according to claim 1 in which said means for promoting diffusion comprises a pump for evacuating the compartment and a first path leading directly from the compartment to the pump, said apparatus further including a second path leading from the compartment to the pump by way of the detector assembly and including said flow path, the second path having a portion of reduced cross-section in the flow path between the compartment and the detector assembly, said temperature maintaining means including valve means in said first path, and means sensing a pressure differential along the reduced cross-section portion of the second path for controlling the valve means to maintain a substantially constant flow rate along the second path to the detector assembly during evacuation of the compartment whereby to maintain the selectively permeable means at said substantially constant temperature.

3. Apparatus according to claim 2 including a vent port in the compartment to allow the pressure in the compartment to stabilise at a lower limit during evacuation of the compartment, said sensing means actuating the valve means to substantially close the first path at said lower pressure limit.

4. Apparatus according to claim 1 in which the means to promote the rapid diffusion of vapours out of the container and into the compartment comprises the combination of oscillatory means in said compartment for vibrating the atmosphere within the compartment and pump means connected to said compartment for evacuating same to a lower pressure limit.

5. Apparatus according to claim 4 in which said oscillatory means operates in a frequency range from subsonic through sonic to ultra-sonic.

6. Apparatus for rapidly checking the contents of closed containers for the presence of substance capable of emitting vapours, comprising:
   a compartment for receiving the containers and having an exhaust port;
   a vacuum pump;
   first relatively high flow rate passage means connecting said vacuum pump to said compartment exhaust port for rapid initial evacuation of said compartment to a lower limit of pressure whereat vapours seeping into the compartment from substances in a said container achieve a maximum concentration in the compartment;
   second relatively low flow rate passage means in parallel with said first passage means and connecting said vacuum pump to said compartment exhaust port, said second passage means including a reduced cross-section portion receiving vapors from said compartment exhaust port, and a detector feed conduit coupled thereto;
   means for maintaining a preselected flow rate through said reduced cross-section portion and including valve means interposed in said first passage means and (1) actuable to an open condition for maximizing the rate of evacuation of said compartment by said vacuum pump until said lower limit of pressure is reached, and (2) thereafter actuable to substantially close said first passage means for causing substantially all the exhaust flow from said compartment through said reduced cross-section portion;
   detector means connected to said detector feed conduit for detecting the presence of vapours of interest passing through said detector feed conduit;
   whereby initial pumping is primarily through said first passage means and rapidly draws vapours from said containers in said compartment to maximize the amount of such vapours in the compartment exhaust, and subsequent pumped flow of compartment exhaust is at least primarily through said second passage means for detection of vapours of interest.

7. Apparatus according to claim 6 including selectively permeable means in said second passage means and coupling said reduced cross-section portion to said detector feed conduit, said selectively permeable means comprising a permeable membrane capable of passing therethrough vapours of interest while substantially blocking passage therethrough of other gases drawn through the second passage means, means for maintaining the permeability of said permeable membrane substantially constant, said permeability maintaining means being responsive to obtaining of said lower limit of pressure for adjusting said valve means to maintain said lower limit of pressure in said reduced cross-section portion, whereby the exhaust gas flow to said permeable membrane is held substantially constant to eliminate temperature variations at said membrane due to flow rate variations and hence to avoid variation in membrane permeability characteristics.

8. Apparatus according to claim 7 in which said permeability maintaining means includes heater compartment means surrounding said membrane for protecting said membrane from fluctuations in ambient temperature, thereby further tending to prevent temperature change induced variations in membrane permeability characteristics and in which said heater compartment means surrounds the reduced cross-section portion of said second passageway means, said membrane and said detector and holds same at an elevated temperature for reducing the possibility of trace gases clinging to interior wall surfaces thereof.

9. Apparatus according to claim 6 including a duct interconnecting a portion of said second passage means, downstream of said membrane, to a point in said detector downstream of said detector feed conduit, enlarged chamber means in said second passage means intermediate said reduced cross-section portion and said duct and housing said membrane loosely therein to permit bypassing of exhaust gas components not of interest around the membrane and downstream along said second passage means to said pump, said duct and said chamber means equalizing the pressure on the upstream and downstream sides of said membrane and avoiding undesirable ballooning and possible bursting of the membrane.

10. Apparatus according to claim 6 in which second passage means includes an enlarged chamber communicating with the downstream end of said reduced cross-section portion and containing said membrane loosely therein, a head member in said chamber having an open end substantially facing said reduced cross-section portion and closed by said membrane, said open end of said head terminating the upstream end of said detector feed conduit for placing same in communication with the downstream face of said membrane and duct means coupled to a carrier gas supply and communicating with the space between the downstream face of said membrane and said open end of said member for providing to said detector a mixture of carrier gas and vapours penetrating said membrane, a downstream portion of said detector being coupled to said vacuum pump for maintaining a flow through said detector from said detector feed conduit.

* * * * *